(12) United States Patent
Manzer

(10) Patent No.: US 6,664,402 B2
(45) Date of Patent: Dec. 16, 2003

(54) MANUFACTURE OF 3-METHYL-TETRAHYDROFURAN FROM ALPHA-METHYLENE-GAMMA-BUTYROLACTONE IN A TWO STEP PROCESS

(75) Inventor: Leo Ernest Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/191,305

(22) Filed: Jul. 9, 2002

(65) Prior Publication Data

US 2003/0109724 A1 Jun. 12, 2003

Related U.S. Application Data

(60) Provisional application No. 60/304,282, filed on Jul. 10, 2001.

(51) Int. Cl.[7] .............................................. C07D 323/02
(52) U.S. Cl. ....................................... 549/429; 549/508
(58) Field of Search ................................. 549/429, 508

(56) References Cited

U.S. PATENT DOCUMENTS 5,990,324 A    11/1999   Takemoto et al.

FOREIGN PATENT DOCUMENTS

| JP | 219981 | 8/1994 |
| JP | 217768 | 8/1996 |

*Primary Examiner*—Amelia Owens

(57) ABSTRACT

Disclosed is a two-step, continuous hydrogenation process for the preparation of 3-methyl-tetrahydrofuran from alpha-methylene-gamma-butyrolactone, which comprises a first step of subjecting alpha-methylene-gamma-butyrolactone to hydrogenation to synthesize 2-methyl-gamma-butyrolactone; and the second step of hydrogenating the 2-methyl-gamma-butyrolactone formed in the first step. The above process enables the production of the objective highly-pure 3-methyl-tetrahydrofuran free from alcohol in high efficiency and high conversion through simple production steps.

19 Claims, No Drawings

MANUFACTURE OF 3-METHYL-TETRAHYDROFURAN FROM ALPHA-METHYLENE-GAMMA-BUTYROLACTONE IN A TWO STEP PROCESS

FIELD OF INVENTION

Described is a continuous process, accomplished in two chemical steps for preparing 3-methyl-tetrahydrofuran a material that can be used as a comonomer in the production of modified poly(tetramethylene glycol), from alpha-methylene-gamma-butyrolactone

BACKGROUND OF THE INVENTION

Substituted tetrahydrofuran like 3-methyl-tetrahydrofuran of the present invention is in general useful in those areas of use of tetrahydrofuran. Examples include polymerization to obtain fibers and uses as a solvent.

Poly (tetra methylene ether glycol) is obtained by polymerization of tetrahydrofuran. This polymer is used as chain segments in polyurethanes and polyesters. Polyurethanes based on poly (tetra methylene ether glycol) soft-segment have improved hydrolytic stability, abrasion resistance and elastomeric properties. Other benefits include strength, toughness, durability, low compression set property, and high water vapor permeability. The largest end-use area is in spandex fibers for apparel. The products containing poly (tetra methylene ether glycol) are used in wheels, high-speed rolls, automotive parts, bushings, specialty hose, cable sheathing and coating, pipeline liners, roof, and floor coatings. The 3-methyl-tetrahydrofuran monomer can be utilized as a comonomer for modifying poly(tetra methylene ether glycol) to yield better elastomeric properties.

In use of tetrahydrofuran as a solvent where lower volatility is desired, 3-methyl-tetrahydrofuran is advantageous because tetrahydrofuran boils at 66° C. whereas 3-methyl-tetrahydrofuran boils at 86° C.

Processes for producing 3-methyl-tetrahydrofuran, by hydrogenation of an itaconic acid ester or a 3-formyl-2-methylpropionic acid ester, and by hydrogenation of a methyl-succinic ester are described in Japanese Patent Applications 219981/1994 and 217768/1996, respectively. Along with the objective 3-methyl-tetrahydrofuran, these reactions produce an alcohol, which has to be separated in a further step. The 3-methyl-tetrahydrofuran forms an azeotropic mixture with most of the lower alcohols, for example, with methanol having an azeotropic point at 64.5° C., and an azeotropic composition consisting of 25% by weight of 3-methyl-tetrahydrofuran and 75% by weight of methanol. The azeotropic distillation requires energy for separating the two components. In particular, the 3-methyl-tetrahydrofuran which is employed for modifying poly(tetramethylene glycol) can tolerate an alcohol impurity of less than 0.2%.

A process for producing 3-methyl-tetrahydrofuran, by hydrogenation of beta-formylisobutyric acid ester with the following general formula is described in U.S. Pat. No. 5,990,324: ROOC—CH(CH$_3$)—CH$_2$—CHO, wherein, R is an alkyl group having 1 to 3 carbon atoms and the formyl group may be present as an acetal having an alkanol with 1 to 8 carbon atoms. In this process, the alcohol is separated from 2-methyl-gamma-butyrolactone in the second step of the three-step process. This separation can be effected by simple distillation. Azeotropic distillation is not required. However, a separation of the alcohol is still a necessary step in the process.

The present invention describes a two-step route to produce 3-methyl-tetrahydrofuran from alpha-methylene-gamma-butyrolactone, without any alcohol production or separation during the two steps.

SUMMARY OF INVENTION

This invention relates to a continuous process for producing 3-methyl-tetrahydrofuran, which comprises the steps of:
(a) subjecting the compound represented by the formula (I), alpha-methylene-gamma-butyrolactone, to hydrogenation to yield 2-methyl-gamma-butyrolactone (II); and
(b) hydrogenating the 2-methyl-gamma-butyrolactone produced in step (a), to yield 3-methyl-tetrahydrofuran (III) as product.

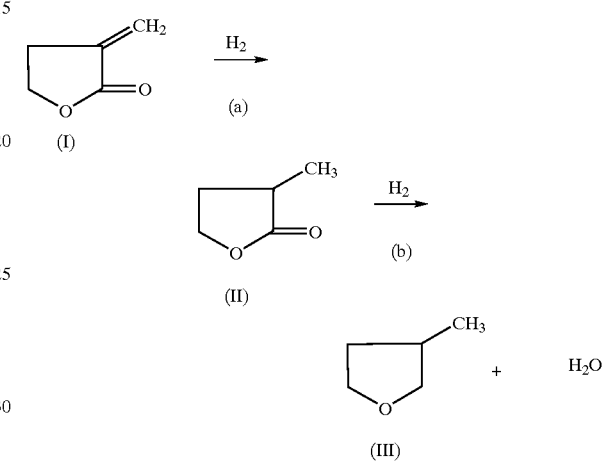

DETAILED DESCRIPTION OF THE INVENTION

By "alpha-methylene-gamma-butyrolactone" is meant the compound described in the formula below.

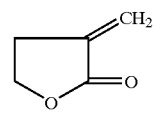

alpha-methylene-gamma-butyrolactone

By "acid promoter" is meant a compound acidic in nature that is added to enhance the physical or chemical function of a catalyst.

By "metal promoter" is meant a metallic compound that is added to enhance the physical or chemical function of a catalyst.

This invention relates to synthesis of 3-methyl-tetrahydrofuran from alpha-methylene-gamma-butyrolactone reactant. More specifically, this invention relates to synthesis of 3-methyl-tetrahydrofuran in a two step continuous process from alpha-methylene-gamma-butyrolactone, which is free from an alcohol as a side product. The final product does not need separation or purification of alcohol. Owing to the high temperature of the catalytic reactions (greater than 150° C.), previous attempts to directly convert alpha-methylene-gamma-butyrolactone to 3-methyl-tetrahydrofuran have resulted in the formation of a polymer of methylene-gamma-butyrolactone monomer. Therefore, an improved process to synthesize 3-methyl-tetrahydrofuran was desired.

A process for making 3-methyl-tetrahydrofuran from an acid-catalyzed, two-step hydrogenation of alpha-methylene-gamma-butyrolactone is disclosed. In a preferred embodiment, the hydrogenation of alpha-methylene-gamma-butyrolactone is carried out in two steps wherein first, alpha-methylene-gamma-butyrolactone is hydrogenated to 2-methyl-gamma-butyrolactone and second, 2-methyl-gamma-butyrolactone is further reduced/hydrogenated to final product.

In the first step of the process, the -methylene double bond of the alpha-methylene-gamma-butyrolactone reactant is hydrogenated to yield 2-methyl-gamma-butyrolactone as the intermediate product. This reaction is carried out under mild conditions to avoid the formation of poly(alpha-methylene-gamma-butyrolactone). A metal catalyst, with or without a support may be present to effect the hydrogenation reaction. An acid material may optionally be used as a promoter to aid the reaction. A metal may also be optionally used as a promoter to aid the reaction.

In the second step of the process, the intermediate product, 2-methyl-gamma-butytrolactone is reduced by hydrogenation to yield 3-methyl-tetrahydrofuran, the desired product. This reaction is carried out at a higher temperature than the first hydrogenation step. A metal catalyst, with or without a support may be present to effect the reduction reaction. An acid system may be used as a promoter to effect the reaction. A metal may also be optionally used as a promoter to aid the reaction.

The process of the present invention may be carried out in batch, sequential batch (i.e., a series of batch reactors) or in continuous mode in any of the equipment customarily employed for continuous process. The condensate water is optionally removed from the reaction mass with the aid of an inert gas purge.

The temperature of the process is controlled in order to achieve a high yield of 2-methyl-gamma-butyrolactone in step (a) and a high yield of 3-methyl-tetrahydrofuran in step (b). Temperature range of from about 90° C. to about 250° is employed in step (a) of the synthesis and temperature range of from about 100° C. to about 250° C., in step (b). A temperature range of from about 135° C. to about 165° C. is preferred in step (a) of the synthesis and a temperature range of from about 200° C. to about 250° C. is preferred in step (b). Another preferred temperature range for step (a) is from about 215° C. to about 240° C. A further preferred range for step (b) is from about 215° C. to about 240° C.

A pressure range of from about 1.0 MPa to about 14.0 MPa is employed in step (a) of the synthesis and pressure range of from about 1.0 MPa to about 15 MPa, in step (b). Pressure range of from about 4.0 MPa to about 8.0 MPa is preferred in step (a) of the synthesis and pressure range of from about 8.0 MPa to about 10.0 MPa is preferred in step (b).

A catalyst is a substance that affects the rate of the reaction but not the reaction equilibrium, and emerges from the process, chemically unchanged. A chemical promoter generally augments the activity of a catalyst. The promoter may be incorporated into the catalyst during any step in the chemical processing of the catalyst constituent. The chemical promoter generally enhances the physical or chemical function of the catalyst agent, but can also be added to retard undesirable side reactions.

Hydrogenation of alpha-methylene-gamma-butyrolactone to 2-methyl-gamma-butyrolactone as disclosed in step (a), is effected in presence of a catalytic metal. The principal component of the catalyst is selected from the group consisting of palladium, ruthenium, rhenium, rhodium, iridium, platinum, compounds thereof, and combinations thereof.

The metal catalyst used in step (a) of the process disclosed may be used as a supported or as an unsupported catalyst. A supported catalyst is one which in which the active catalyst agent is deposited on a support material by spraying, soaking or physical mixing, followed by drying, calcination, and if necessary, activation through methods such as reduction or oxidation. Materials frequently used as support are porous solids with high total surface areas (external and internal) which can provide high concentrations of active sites per unit weight of catalyst. The catalyst support may enhance the function of the catalyst agent. A catalyst which is not supported on a catalyst support material is an unsupported catalyst. A support material is selected from the group consisting of carbon, alumina, silica, silica-alumina, titania, and a combination thereof. Moreover, supported catalytic metal/s may have the same supporting material or different supporting material. A more preferred support is carbon. The carbon can be a commercially available carbon such as Calsicat C, Sibunit C, or Calgon C (under the trade name Centaur(R)).

A preferred catalytic metal content range of the supported catalyst is from about 0.1% to about 15%. A more preferred catalytic metal content range is from about 1% to about 7%. A further preferred catalytic metal content range is from about 1% to about 5%.

Preferred combinations of catalytic metal and support system includes palladium on carbon, palladium on silica, ruthenium on carbon, ruthenium on alumina, rhodium on carbon, and rhodium on alumina.

An acid promoter may be used in step (a) of synthesis in the present invention. Suitable promoters include, those acids with a pKa less than about 4, preferably with a pKa less than about 2, including inorganic acids, organic sulfonic acids, heteropolyacids, perfluoroalkylsulfonic acids, and mixtures thereof. Also suitable are metal salts of acids with pKa less than about 4, including metal sulfonates, metal trifluoroacetates, metal triflates, and mixtures thereof including mixtures of salts with their conjugate acids. Specific examples of promoters include sulfuric acid, fluorosulfonic acid, phosphoric acid, p-toluenesulfonic acid, benzenesulfonic acid, phosphotungtstic acid, phosphomolybdic acid, trifluromethanesulfonic acid, 1,1,2,2-tetrafluroethanesulfonic acid, 1,2,3,2,3,3-hexapropanesulfonic acid, bismuth triflate, yttrium triflate, ytterbium triflate, neodymium triflate, lanthanum triflate, scandium triflate, and zirconium triflate. A preferred promoter is selected from $Zn(BF_4)_2$ or CBV-3020 zeolite. The acid promoter is used in concentration of from 0.1% to 5% by weight of the reactant. A preferred concentration range is 0.25% to 2.5% by weight of the reactant.

Suitable heterogeneous acid promoters are zeolites, fluorinated alumina, acid-treated silica, acid treated silica-alumina, acid treated clays, heterogeneous heteropolyacids and sulfated zirconia.

A metal promoter may be used optionally with the acid promoter in reaction of the present invention. Suitable metal promoters include tin, zinc, copper, gold, silver, and combinations thereof. The preferred metal promoter is tin. Reduction of 2-methyl-gamma-butyrolactone to 3-methyl-tetrahydrofuran product and water as disclosed in step (b), is effected in presence of a metal catalyst. The catalytic metal component of the catalyst is selected from the group consisting of metals of Group 7, 8, 9, 10, of the Periodic Table, compounds of a metal of group 7, 8, 9, 10 of the Periodic Table, compounds thereof, combinations thereof, copper, and copper compounds.

The catalytic metal used in step (b) of the process disclosed here may be used as supported or an unsupported catalyst. A support material is selected from the group consisting of carbon, alumina, silica, silica-alumina, titania, and a combination thereof. Moreover, supported catalytic metal/s may have the same supporting material or different supporting material. A more preferred support is carbon. The carbon can be a commercially available carbon such as Calsicat C, Sibunit C, or Calgon C (Centaur(R)).

A preferred catalytic metal content range is from about 0.1% to about 25%. A more preferred catalytic metal content range is from about 1% to about 7%, and a further preferred catalytic metal content range is from about 1% to about 5%. Another preferred catalytic metal content is range is from about 18% to about 22%.

A preferred combination of catalytic metal and support system includes rhodium on carbon, rhenium on carbon, rhenium on alumina, iridium on carbon, iridium on alumina, ruthenium on alumina, and a combination of (ruthenium+ rhenium) on carbon.

An acid promoter may be used in step (b) of synthesis in the present invention. Suitable promoters include, those acids with a pKa less than about 4, preferably with a pKa less than about 2, including inorganic acids, organic sulfonic acids, heteropolyacids, perfluoroalkylsulfonic acids, and mixtures thereof. Also suitable are metal salts of acids with pKa less than about 4, including metal sulfonates, metal trifluoroacetates, metal triflates, and mixtures thereof including mixtures of salts with their conjugate acids. Specific examples of promoters include sulfuric acid, fluorosulfonic acid, phosphoric acid, p-toluenesulfonic acid, benzenesulfonic acid, phosphotungtstic acid, phosphomolybdic acid, trifluromethanesulfonic acid, 1, 1, 2, 2-tetrafluroethanesulfonic acid, 1, 2, 3, 2, 3, 3-hexapropanesulfonic acid, bismuth triflate, yttrium triflate, ytterbium triflate, neodymium triflate, lanthanum triflate, scandium triflate, and zirconium triflate. A preferred promoter is selected from group consisting of $Zn(BF4)_2$, zeolite CBV-1502, zeolite 20A, zeolite CBV 3020E, 13% Nafion(R), and methane sulfonic acid. The acid promoter is used in concentration of from 0.1% to 5% by weight. A preferred concentration range is 0.25% to 2.5%.

Suitable heterogeneous promoters are zeolites, fluorinated alumina, acid-treated silica, acid treated silica-alumina, acid treated clays, heterogeneous heteropolyacids and sulfated zirconia.

A metal promoter may be used optionally with the acid promoter in reaction of the present invention. Suitable metal promoters include tin, zinc, copper, gold, silver, and combinations thereof. A preferred metal promoter is tin.

EXPERIMENTAL

The following abbreviations are used in the Examples:

| | |
|---|---|
| ESCAT | Series of catalysts provided by Engelhard Corp. |
| Calsicat Carbon | Catalyst support from Engelhard Corp. |
| Sibunit Carbon | Catalyst support from Inst. of Technical Carbon, Omsk, Russia |
| JM-A11108 Carbon | Catalyst support from Johnson Matthey, Inc. |
| Calgon Carbon | Catalyst support from Calgon Corp. under the brand name of Centaur(R) |
| CBV-3020E | Type of Zeolite acid promoter |
| 20-A | Type of Zeolite acid promoter |
| CBV-1502 | Type of Zeolite acid promoter |

A commercially available support such as carbon, alumina, silica, silica-alumina, titania available from Engelhard Corp. (E. Windsor, Conn.) was impregnated by incipient wetness with a metal salt. The precursors used were $NiCl_2.6H_2O$ (Alfa Chemical Co.), $Re_2O_7$ (Alfa Chemical Co.), $PdCl_2$ (Alfa Chemical Co.), $RuCl_3.xH_2O$ (Aldrich Chemical Co.). $H_2PtCl_6$ (Johnson Matthey, Inc., W. Deptford, N.J.), $CrCl_3.6H_2O$ (Mallinckrodt Baker, Inc.), 5% Rh using $RhCl_3.xH_2O$ (Alfa Chemical Co.). The samples were dried and reduced at 300–450° C. in $H_2$ for 2 hours.

The carbon used was commercially available as Calsicat Carbon, Sibunit Carbon, or Calgon Carbon (Centaur(R)). Calsicat Carbon is lot S-96-140 from Engelhard Corp., Beachwood, Ohio. Sibunit Carbon is Sibunit-2 from Institute of Technical Carbon, 5th Kordnaya, Omsk 64418, Russia. Calgon Carbon is PCB Carbon from Calgon Corp. (under the registered trademark of Centaur(R)).

Example-1

Catalyst Preparation 5% Pt on Acid Washed Calsicat Carbon

In a 150 ml beaker, a solution was made up of 4.5 ml, 0.3 M $H_2PtCl_6$ with 4.0 ml deionized $H_2O$. To the beaker were added 4.75 g Calsicat Acid Washed Carbon (12×20 mesh, dried at 120° C. overnight). The slurry was allowed to stand at room temperature for 1 hr with occasional stirring and then dried at 120° C. overnight with frequent stirring (until free flowing).

In an alumina boat, in a quartz lined tube furnace, the catalyst was purged with 500 SCCM $N_2$ at room temperature for 15 min and then with 100 SCCM He at room temperature for 15 min. The catalyst was heated to 150° C. and held at 150° C. under He for 1 hr. At this point, 100 SCCM $H_2$ were added and the sample was held at 150° C. under He and $H_2$ for 1 hr. The temperature was increased to 300° C. and the catalyst was reduced at 300° C. under He—$H_2$ for 8 hrs. The $H_2$ was stopped, the sample was held at 300° C. under He for 30 min and then cooled to room temperature in flowing He. The catalyst was finally passivated in 1.5% $O_2$ in $N_2$ at 500 SCCM for 1 hour at room temperature and weighed 4.93 grams when unloaded.

Examples 1–52

Hydrogenation of Alpha-Methylene-Gamma-Butyrolactone to 2-Methyl-Gamma-Butyrolactone-Step (a)

50% alpha-methylene-gamma-butyrolactone in Dioxane (974.7 mg, 5.0 mmole) and an amount of catalyst with a support as indicated in Table 1, were added to a 2 ml batch reactor. The reactor was sealed and charged with pressure of $H_2$ at 6.89 MPa for examples 1–8, and 23–26, 4.82 MPa for 14–22 and 27–52, and 1.38 MPa for 9–13, and heated to reaction temperature of 225° C. for examples 1–8, and 23–26, and 150° C. for 12–22 and 27–52, and 100° C. for 9–11. The reaction was stopped after 2 hours for examples 1–7, and 23–52, and at 4 hours for examples 8–22 and rapidly cooled. An internal standard (2-methoxy ethyl ether) was added into the reaction mixture and GC analysis was performed on a HP-6890 GC with a Chrompack column (CP-WAX 58, 25 M×0.25 MM). The following table lists the reaction conditions catalyst, acid promoter and conversion and selectivity of the reactant and products, respectively. All experiments were conducted with a 50% a-alpha-methylene-gamma-butyrolactone in dioxane.

TABLE 1

| Ex. No. | Time (hrs) | Temp (° C.) | H₂ Pressure (MPa) | Catalyst/Support | Acid | α-MBL Conversion % | 2-Me-GBL Selectivity % | 3-Me-THF Selectivity % |
|---|---|---|---|---|---|---|---|---|
| 1. | 2 | 225 | 6.89 | 5% Pd/C(ESCAT 140) | 0 | 99.21 | 83.53 | 0.23 |
| 2. | 2 | 225 | 6.89 | 5% Pd/C(ESCAT 142) | 0 | 85.57 | 93.72 | 0.28 |
| 3. | 2 | 225 | 6.89 | 5% Pd/C(ESCAT 143) | 0 | 99.49 | 96.94 | 0.19 |
| 4 | 2 | 225 | 6.89 | 5% Pd/C(ESCAT 148) | 0 | 86.71 | 97.80 | 0.33 |
| 5. | 2 | 225 | 6.89 | 5% Pd/C(ESCAT 149) | 0 | 99.92 | 94.36 | 0.14 |
| 6. | 2 | 225 | 6.89 | 5% Pd/C(ESCAT 160) | 0 | 95.05 | 97.80 | 0.24 |
| 7. | 2 | 225 | 6.89 | 5% Pd/C(ESCAT 162) | 0 | 97.87 | 88.55 | 0.15 |
| 8. | 4 | 225 | 6.89 | 5% Ru/Al₂O₃ + 5% Ir/Al₂O₃ | 0 | 98.33 | 68.52 | 0.17 |
| 9. | 4 | 100 | 1.38 | 5% Pd/C(JM-A11208-5) | 0 | 100.00 | 0.00 | 0.00 |
| 10. | 4 | 100 | 1.38 | 5% Pd/C(JM-A11108-5) | 0 | 56.47 | 67.70 | 0.00 |
| 11. | 4 | 100 | 1.38 | 5% Pd/C(JM-A11208-5) | 0 | 65.22 | 47.97 | 0.00 |
| 12. | 4 | 150 | 1.38 | 5% Pd/C(JM-A11108-5) | 0 | 48.24 | 96.37 | 0.00 |
| 13. | 4 | 150 | 1.38 | 5% Pd/C(JM-A11208-5) | 0 | 53.23 | 76.40 | 0.00 |
| 14. | 4 | 150 | 4.82 | 5% Pd/C(JM-A11108-5) | 0 | 86.98 | 97.46 | 0.00 |
| 15. | 4 | 150 | 4.82 | 5% Pd/C(JM-A11208-5) | 0 | 90.80 | 86.76 | 0.00 |
| 16. | 4 | 150 | 4.82 | 5% Pd/C(ESCAT 140) | 0 | 99.32 | 94.44 | 0.00 |
| 17. | 4 | 150 | 4.82 | 5% Pd/C(ESCAT 142) | 0 | 98.66 | 90.84 | 0.00 |
| 18. | 4 | 150 | 4.82 | 5% Pd/C(ESCAT 143) | 0 | 98.76 | 91.10 | 0.00 |
| 19. | 4 | 150 | 4.82 | 5% Pd/C(ESCAT 148) | 0 | 94.99 | 89.87 | 0.00 |
| 20. | 4 | 150 | 4.82 | 5% Pd/C(ESCAT 149) | 0 | 99.94 | 86.35 | 0.00 |
| 21. | 4 | 150 | 4.82 | 5% Pd/C(ESCAT 160) | 0 | 96.16 | 84.32 | 0.00 |
| 22. | 4 | 150 | 4.82 | 5% Pd/C(ESCAT 162) | 0 | 99.64 | 86.08 | 0.00 |
| 23. | 2 | 225 | 6.89 | 1% Ru/6% Re/C | 0 | 99.44 | 90.27 | 0.16 |
| 24. | 2 | 225 | 6.89 | 1.87% Ru/5.65% Re/0.77% Sn/C | 0 | 83.75 | 7.10 | 0.00 |
| 25. | 2 | 225 | 6.89 | 1.87% Ru/5.65% Re/0.77% Sn/C | Zn(BF₄)₂ | 78.25 | 51.03 | 0.46 |
| 26. | 2 | 225 | 6.89 | 1.87% Ru/5.65% Re/0.77% Sn/C | CBV-3020 | 96.76 | 1.14 | 0.06 |
| 27. | 2 | 150 | 4.82 | 5% Ru/Calsicat C | 0 | 100.00 | 98.45 | 0.00 |
| 28. | 2 | 150 | 4.82 | 5% Ru/Al₂O₃ | 0 | 100.00 | 96.77 | 0.00 |
| 29. | 2 | 150 | 4.82 | 5% Ru/SiO₂ | 0 | 70.47 | 77.90 | 0.00 |
| 30. | 2 | 150 | 4.82 | 5% Rh/Calsicat C | 0 | 100.00 | 95.24 | 0.00 |
| 31. | 2 | 150 | 4.82 | 5% Rh/Al₂O₃ | 0 | 100.00 | 94.30 | 0.00 |
| 32. | 2 | 150 | 4.82 | 5% Rh/SiO₂ | 0 | 71.09 | 57.66 | 0.00 |
| 33. | 2 | 150 | 4.82 | 5% Pd/Calsicat C | 0 | 100.00 | 98.35 | 0.00 |
| 34. | 2 | 150 | 4.82 | 5% Pd/Al₂O₃ | 0 | 86.66 | 94.31 | 0.00 |
| 35. | 2 | 150 | 4.82 | 5% Pd/SiO₂ | 0 | 100.00 | 93.50 | 0.00 |
| 36. | 2 | 150 | 4.82 | 5% Ir/Calsicat C | 0 | 60.94 | 66.85 | 0.00 |
| 37. | 2 | 150 | 4.82 | 5% Ir/Al₂O₃ | 0 | 68.01 | 58.23 | 0.00 |
| 38. | 2 | 150 | 4.82 | 5% Ir/SiO₂ | 0 | 65.92 | 66.74 | 0.00 |
| 39. | 2 | 150 | 4.82 | 5% Pt/Sibunit C | 0 | 91.57 | 93.37 | 0.00 |
| 40. | 2 | 150 | 4.82 | 5% Pt/Al₂O₃ | 0 | 59.61 | 88.22 | 0.00 |
| 41. | 2 | 150 | 4.82 | 5% Pt/C ESCAT-248 | 0 | 74.49 | 97.88 | 0.00 |
| 42. | 2 | 150 | 4.82 | 5% Pt/C ESCAT-268 | 0 | 79.67 | 98.05 | 0.00 |
| 43. | 2 | 150 | 4.82 | 5% Pt/Al2O3 ESCAT-294 | 0 | 43.30 | 94.61 | 0.00 |
| 44. | 2 | 150 | 4.82 | 5% Pt/C JM-B21142-5 | 0 | 64.07 | 95.02 | 0.00 |
| 45. | 2 | 150 | 4.82 | 5% Pt/C JM-B21142-5 | 0 | 68.64 | 99.88 | 0.00 |
| 46. | 2 | 150 | 4.82 | 10% Pt/C | 0 | 27.97 | 82.60 | 0.00 |
| 47. | 2 | 150 | 4.82 | 5% Ru/Calsicat C | 0 | 99.75 | 85.32 | 0.00 |
| 48. | 2 | 150 | 4.82 | 5% Ru/Al₂O₃ | 0 | 100.00 | 78.08 | 0.00 |
| 49. | 2 | 150 | 4.82 | 5% Rh/Calsicat C | 0 | 100.00 | 82.62 | 0.00 |
| 50. | 2 | 150 | 4.82 | 5% Rh/Al₂O₃ | 0 | 100.00 | 74.50 | 0.00 |
| 51. | 2 | 150 | 4.82 | 5% Pd/Calsicat C | 0 | 100.00 | 79.99 | 0.00 |
| 52. | 2 | 150 | 6.89 | 5% Pd/Al₂O₃ | 0 | 100.00 | 73.96 | 0.00 |

Examples 53–116

Reduction of 2-Methyl-Gamma-Butyrolactone to 3-Methyl-Tetrahydrofuran-Step (b)

50% 2-methyl-γ-butyrolactone in dioxane (970.0 mg, 4.84 mmole) and an amount of catalyst and support as indicated in Table 2 were added to a 2 ml batch reactor. The reactor was sealed and charged with 6.89 MPa of H₂, and heated to 225° C., and then cooled rapidly. The reaction was stopped after 4 hours. An internal standard (2-methoxy ethyl ether) was added to the reaction mixture and GC analysis was performed on a HP-6890 GC with a Chrompack column (CP-WAX 58, 25 M×0.25 MM). An acid promoter was not used for examples 53–85. An acid promoter was used for examples 86–116.

TABLE 2

EXAMPLES 53–85

| Ex. No. | Time (hrs) | Temp. (° C.) | $H_2$ Pressure (MPa) | Catalyst/Support | Acid | 2-Me-GBL Conversion (%) | 3-MeTHF Selectivity (%) |
|---|---|---|---|---|---|---|---|
| 53. | 4 | 225 | 6.89 | 1% Ru/6% Re/C | | 19.56 | 49.12 |
| 54. | 4 | 225 | 6.89 | 5% Rh/Sibunit C | | 9.21 | 12.76 |
| 55. | 4 | 225 | 6.89 | 5% Pt/Sibunit C | | 2.12 | 29.23 |
| 56. | 4 | 225 | 6.89 | 5% Ru/Calsicat C | | 9.87 | 77.56 |
| 57. | 4 | 225 | 6.89 | 5% Rh/Calsicat C | | 5.12 | 91.38 |
| 58. | 4 | 225 | 6.89 | 5% Pd/Calsicat C | | 2.44 | 70.21 |
| 59. | 4 | 225 | 6.89 | 5% Re/Calsicat C | | 31.24 | 97.91 |
| 60. | 4 | 225 | 6.89 | 5% Ir/Calsicat C | | 8.95 | 92.01 |
| 61. | 4 | 225 | 6.89 | 5% Pt/Sibunit C | | 2.40 | 82.19 |
| 62. | 4 | 225 | 6.89 | 5% Ru/$Al_2O_3$ | | 1.60 | 95.57 |
| 63. | 4 | 225 | 6.89 | 5% Rh/$Al_2O_3$ | | 26.60 | 3.45 |
| 64. | 4 | 225 | 6.89 | 5% Pd/$Al_2O_3$ | | 88.01 | 0.80 |
| 65. | 4 | 225 | 6.89 | 5% Re/$Al_2O_3$ | | 7.33 | 97.75 |
| 66. | 4 | 225 | 6.89 | 5% Ir/$Al_2O_3$ | | 2.00 | 96.21 |
| 67. | 4 | 225 | 6.89 | 5% Pt/$Al_2O_3$ | | 10.62 | 24.69 |
| 68. | 4 | 225 | 6.89 | 5% Ru/$SiO_2$ | | 5.50 | 10.01 |
| 69. | 4 | 225 | 6.89 | 5% Rh/$SiO_2$ | | 19.51 | 1.67 |
| 70. | 4 | 225 | 6.89 | 5% Pd/$SiO_2$ | | 31.30 | 1.23 |
| 71. | 4 | 225 | 6.89 | 5% Re/$SiO_2$ | | 8.46 | 41.56 |
| 72. | 4 | 225 | 6.89 | 5% Ir/$SiO_2$ | | 1.83 | 31.17 |
| 73. | 4 | 225 | 6.89 | 5% Pt/$SiO_2$ | | 17.41 | 3.50 |
| 74. | 4 | 225 | 6.89 | 5% Re/Sibunit C | | 32.87 | 53.09 |
| 75. | 4 | 225 | 6.89 | 5% Re/Calgon C | | 14.50 | 31.75 |
| 76. | 4 | 225 | 6.89 | 5% Re/Sibunit C(400C) | | 42.45 | 31.39 |
| 77. | 4 | 225 | 6.89 | 5% Re/Sibunit C(450C) | | 24.33 | 46.33 |
| 78. | 4 | 225 | 6.89 | 10% Re/Sibunit C(400C) | | 36.34 | 35.26 |
| 79. | 4 | 225 | 6.89 | 10% Re/Sibunit C(450C) | | 44.95 | 30.02 |
| 80. | 4 | 225 | 6.89 | 5% Re/Calsicat C(400C) | | 36.24 | 94.20 |
| 81. | 4 | 225 | 6.89 | 5% Re/Calsicat C(450C) | | 35.77 | 91.63 |
| 82. | 4 | 225 | 6.89 | 10% Re/Calsicat C(400C) | | 46.13 | 90.11 |
| 83. | 4 | 225 | 6.89 | 10% Re/Calsicat C(450C) | | 49.41 | 91.19 |
| 84. | 4 | 225 | 6.89 | 20% Re/Calsicat C(400C) | | 64.74 | 86.26 |
| 85. | 4 | 225 | 6.89 | 20% Re/Calsicat C(450C) | | 72.11 | 78.25 |

TABLE 3

EXAMPLES 86–116

| Ex. No. | Time (hrs) | Temp. (° C.) | $H_2$ Pressure (MPa) | Catalyst/Support | Acid | 2-Me-GBL Conversion (%) | 3-Me-THF Selectivity (%) |
|---|---|---|---|---|---|---|---|
| 86. | 4 | 225 | 6.89 | 1% Ru/6% Re/C | Zn(BF4)2 | 18.68 | 80.61 |
| 87. | 4 | 225 | 6.89 | 1% Ru/6% Re/C | CBV-1502 | 10.94 | 89.96 |
| 88. | 4 | 225 | 6.89 | 1% Ru/6% Re/C | 20A | 2.70 | 48.33 |
| 89. | 4 | 225 | 6.89 | 5% Rh/Sibunit C | Zn(BF4)2 | 6.15 | 6.79 |
| 90. | 4 | 225 | 6.89 | 5% Rh/Sibunit C | CBV-1502 | 2.21 | 40.48 |
| 91. | 4 | 225 | 6.89 | 5% Pt/Sibunit C | Zn(BF4)2 | 1.37 | 31.66 |
| 92. | 4 | 225 | 6.89 | 5% Pt/Sibunit C | CBV-1502 | 4.83 | 6.35 |
| 93. | 4 | 225 | 6.89 | 5% Pd/Calsicat C | Zn(BF4)2 | 10.08 | 92.06 |
| 94. | 4 | 225 | 6.89 | 5% Pd/Calsicat C | CBV-3020E | 4.75 | 8.31 |
| 95. | 4 | 225 | 6.89 | 5% Pd/Calsicat C | 13% NAFION | 1.37 | 18.57 |
| 96. | 4 | 225 | 6.89 | 5% Pd/Calsicat C | MSA | 2.48 | 11.71 |
| 97. | 4 | 225 | 6.89 | 5% Ru/Calsicat C | Zn(BF4)2 | 6.90 | 86.35 |
| 98. | 4 | 225 | 6.89 | 5% Ru/Calsicat C | CBV-3020E | 3.16 | 62.88 |
| 99. | 4 | 225 | 6.89 | 5% Ru/Calsicat C | 13% NAFION(R) | 6.11 | 57.65 |

TABLE 3-continued

EXAMPLES 86–116

| Ex. No. | Time (hrs) | Temp. (° C.) | H₂ Pressure (MPa) | Catalyst/Support | Acid | 2-Me-GBL Conversion (%) | 3-Me-THF Selectivity (%) |
|---|---|---|---|---|---|---|---|
| 100. | 4 | 225 | 6.89 | 5% Ru/Calsicat C | MSA | 8.59 | 32.53 |
| 101. | 4 | 225 | 6.89 | 5% Re/Calsicat C | Zn(BF4)2 | 4.07 | 72.97 |
| 102. | 4 | 225 | 6.89 | 5% Re/Calsicat C | CBV-3020E | 8.42 | 79.78 |
| 103. | 4 | 225 | 6.89 | 5% Re/Calsicat C | 13% NAFION(R) | 10.21 | 91.35 |
| 104. | 4 | 225 | 6.89 | 5% Re/Calsicat C | MSA | 16.03 | 92.79 |
| 105. | 4 | 225 | 6.89 | 5% Rh/Calsicat C | Zn(BF4)2 | 0.69 | 57.72 |
| 106. | 4 | 225 | 6.89 | 5% Rh/Calsicat C | CBV-3020E | 1.01 | 70.50 |
| 107. | 4 | 225 | 6.89 | 5% Rh/Calsicat C | 13% NAFION(R) | 1.14 | 42.94 |
| 108. | 4 | 225 | 6.89 | 5% Rh/Calsicat C | MSA | 2.34 | 38.14 |
| 109. | 4 | 225 | 6.89 | 5% Pt/Sibunit C | Zn(BF4)2 | 2.01 | 35.66 |
| 110. | 4 | 225 | 6.89 | 5% Pt/Sibunit C | CBV-3020E | 0.61 | 31.75 |
| 111. | 4 | 225 | 6.89 | 5% Pt/Sibunit C | 13% NAFION | 2.07 | 30.65 |
| 112. | 4 | 225 | 6.89 | 5% Pt/Sibunit C | MSA | 2.67 | 24.09 |
| 113. | 4 | 225 | 6.89 | 5% Ir/Calsicat C | Zn(BF4)2 | 1.39 | 71.80 |
| 114. | 4 | 225 | 6.89 | 5% Ir/Calsicat C | CBV-3020E | 2.63 | 54.40 |
| 115. | 4 | 225 | 6.89 | 5% Ir/Calsicat C | 13% NAFION(R) | 1.77 | 63.55 |
| 116. | 4 | 225 | 6.89 | 5% Ir/Calsicat C | MSA | 3.03 | 55.50 |

What is claimed is:

1. A continuous process for producing 3-methyl-tetrahydrofuran comprising the steps of:
   (a) hydrogenating the compound alpha-methylene-gamma-butyrolactone, represented by the formula (I) in the presence of a first catalytic metal and optionally in the presence of a first catalyst promoter, to produce 2-methyl-gamma-butyrolactone; and
   (b) hydrogenating the compound 2-methyl-gamma-butytrolactone, represented by formula (II), produced in step (a), in the presence of a second catalytic metal and optionally in the presence of a second catalyst promoter;

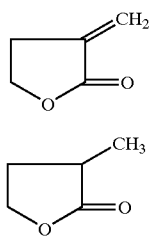

wherein the first catalytic metal is optionally supported and is selected from the group consisting of palladium, ruthenium, rhenium, rhodium, iridium, platinum, compounds thereof, and combinations thereof;
wherein the second catalytic metal is optionally supported and is selected from a group consisting of copper, cobalt, nickel, iron, rhenium, palladium, ruthenium, platinum, rhodium, manganese, iridium, technetium, osmium, gold, compounds thereof, and combinations thereof; and
wherein, said first and said second catalyst promoters are independently selected from the group consisting of tin, zinc, copper, gold, silver, sulfuric acid, fluorosulfonic acid, phosphoric acid, p-toluenesulfonic acid, benzenesulfonic acid, phosphotungtstic acid, phosphomolybdic acid, trifluromethanesulfonic acid, 1,1,2,2-tetrafluorethanesulfonic acid, 1,1,1,2,3,4-hexafluorpropanesulfonic acid, bismuth triflate, yttrium triflate, ytterbium triflate neodymium triflate, lanthanum triflate, scandium triflate, zirconium triflate, heteropolyacids supported on zirconia, titania, $Zn(BF_4)_2$, methane sulfonic acid and Nafion®.

2. The process as recited in claim 1, wherein the first catalytic metal is supported on a catalyst support selected from the group consisting of carbon, alumina, silica, silica-alumina, titania, compounds thereof, and combinations thereof.

3. The process as recited in claim 1, wherein the second catalytic metal is supported on a catalyst support selected from the group consisting of carbon. alumina, silica, silica-alumina, titania, and combinations thereof.

4. The process as recited in claim 1, wherein step (a) is performed at a temperature from about 90° C. to about 250° C.

5. The process as recited in claim 1, wherein step (a) is performed at a temperature from about 135° C. to about 165° C.

6. The process as recited in claim 1, wherein step (a) is performed at a temperature from about 215° C. to about 240° C.

7. The process as recited in claim 1, wherein step (b) is performed at a temperature from about 100° C. to about 250° C.

8. The process as recited in claim 1, wherein step (b) is performed at a temperature from about 200° C. to about 250° C.

9. The process as recited in claim 1, wherein step (b) is preformed at a temperature from about 215° C. to about 240° C.

10. The process as recited in claim 1, wherein step (a) is performed at a pressure from about 1.0 MPa to about 14.0 MPa.

11. The process as recited in claim 1, wherein step (a) is performed at a pressure from about 4.0 MPa to about 8.0 MPa.

12. The process as recited in claim 1, wherein step (b) is performed at a pressure from about 1.0 MPa to about 15.0 MPa.

13. The process as recited in claim 12, wherein step (b) is performed at a pressure from about 8.0 MPa to about 10.0 MPa.

14. The process as recited in claim 1, wherein step (a) is performed at a temperature from about 135° C. to about 165° C. and at a pressure from about 40 MPa to about 8.0 MPa; and step (b) is performed at a temperature from about 215° C. to about 250° C. and at a pressure from about 8.0 MPa to about 10.0 MPa.

15. The process as recited in claim 1, wherein step (a) is performed at a temperature from about 215° C. to about 240° C. and at a pressure from about 4.0 MPa to about 8.0 MPa and step (b) is performed at a temperature from about 215° C. to about 250° C. and at a pressure from about 8.0 MPa to about 10.0 MPa.

16. The process as recited in claim 14 or in claim 15, wherein the first catalytic metal is supported on a first catalytic metal support and the first catalytic metal support is selected from the group consisting of Pd/C, Ru/C, Ru/Al$_2$O$_3$, Rh/C, Rh/Al$_2$O$_3$, and Pd/SiO$_2$; and the second catalytic metal is supported on a second catalytic metal support and the second catalytic metal support is Re/C.

17. The process as recited in claim 14, wherein the first catalytic metal is supported on a first catalytic metal support and the first catalytic metal support is selected from the group consisting of 5% Pd/C, 5% Ru/C, 5% Ru/Al$_2$O$_3$, 5% Rh/C, 5% Rh/Al$_2$O$_3$, and 5% Pd/SiO$_2$; and the second catalytic metal is supported on a second catalytic metal support and the second catalytic metal support is selected from 5% Re/C, 10% Re/C and 20% Re/C.

18. The process as recited in claim 14, wherein the first catalytic metal is supported on a first catalytic metal support and the first catalytic metal support is selected from the group consisting of 5% Pd/C, and (1% Ru/6% Re)/C; and the second catalytic metal is supported on a second catalytic metal support and the second catalytic metal support is selected from 5% Re/C, 10% Re/C and 20% Re/C.

19. The process as recited in claim 1, wherein the second catalytic metal is copper chromite.

* * * * *